(12) United States Patent
Lee et al.

(10) Patent No.: US 10,180,405 B2
(45) Date of Patent: Jan. 15, 2019

(54) METHOD FOR QUANTITATIVE ANALYSIS OF HEAVY METALS

(71) Applicant: AMOREPACIFIC CORPORATION, Seoul (KR)

(72) Inventors: So Mi Lee, Yongin-si (KR); Boo Min Kim, Yongin-si (KR); Na Ri Cha, Yongin-si (KR); Hye Sun Yoo, Yongin-si (KR); Kyoung Hee Byoun, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 62 days.

(21) Appl. No.: 14/932,096

(22) Filed: Nov. 4, 2015

(65) Prior Publication Data
US 2016/0123910 A1     May 5, 2016

(30) Foreign Application Priority Data

| Nov. 4, 2014 | (KR) | 10-2014-0152128 |
| Nov. 4, 2014 | (KR) | 10-2014-0152129 |
| Nov. 4, 2014 | (KR) | 10-2014-0152130 |
| Nov. 4, 2014 | (KR) | 10-2014-0152131 |

(51) Int. Cl.
*G01N 23/223*     (2006.01)
*G01N 23/2202*    (2018.01)
*G01N 33/20*      (2006.01)

(52) U.S. Cl.
CPC ....... *G01N 23/223* (2013.01); *G01N 23/2202* (2013.01); *G01N 33/20* (2013.01)

(58) Field of Classification Search
CPC .... G01N 23/00; G01N 23/22; G01N 23/2202; G01N 23/223; G01N 23/12; G01N 2223/07; G01N 2223/076
USPC ..................................................... 378/44–48
See application file for complete search history.

(56) References Cited

U.S. PATENT DOCUMENTS 5,020,084 A * 5/1991 Robertson ............ G01N 23/223
378/156

* cited by examiner

*Primary Examiner* — Jurie Yun
(74) *Attorney, Agent, or Firm* — Nixon & Vanderhye, P.C.

(57) ABSTRACT

Disclosed is a method for quantitative analysis of heavy metals, particularly lead, arsenic, antimony or cadmium, in a liquid sample. Also disclosed is a method for quantitative analysis of heavy metals, particularly lead, arsenic, antimony or cadmium, in a powdery sample.

15 Claims, 10 Drawing Sheets

[Figure 3]
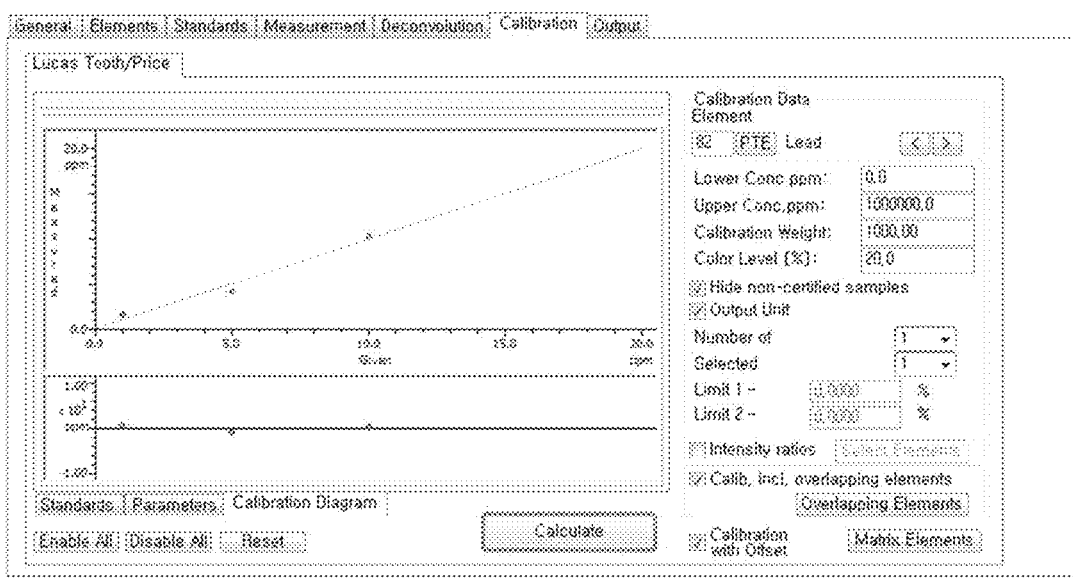
[Figure 4]
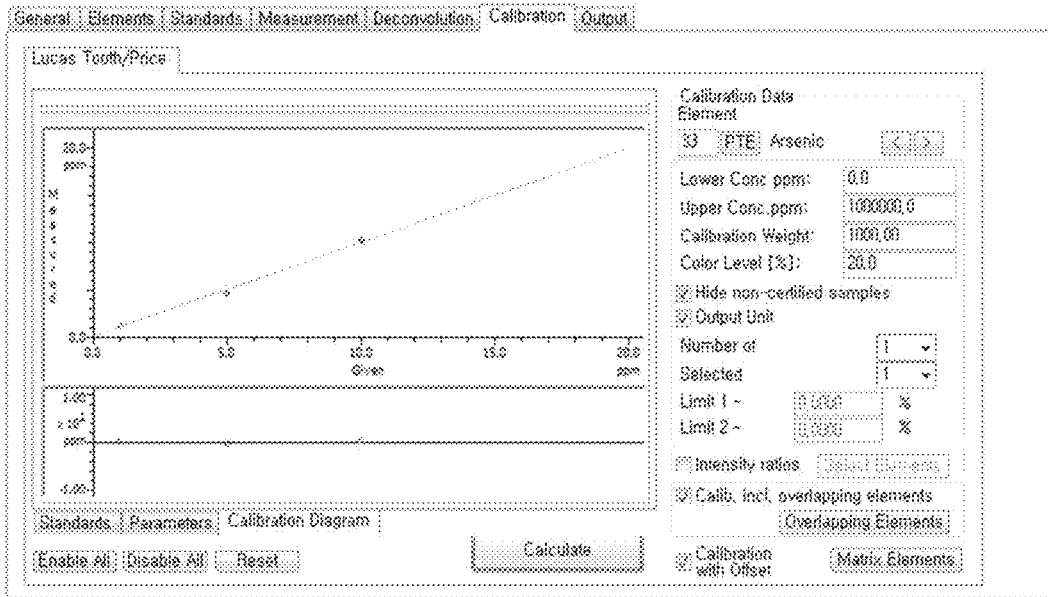

[Figure 5]
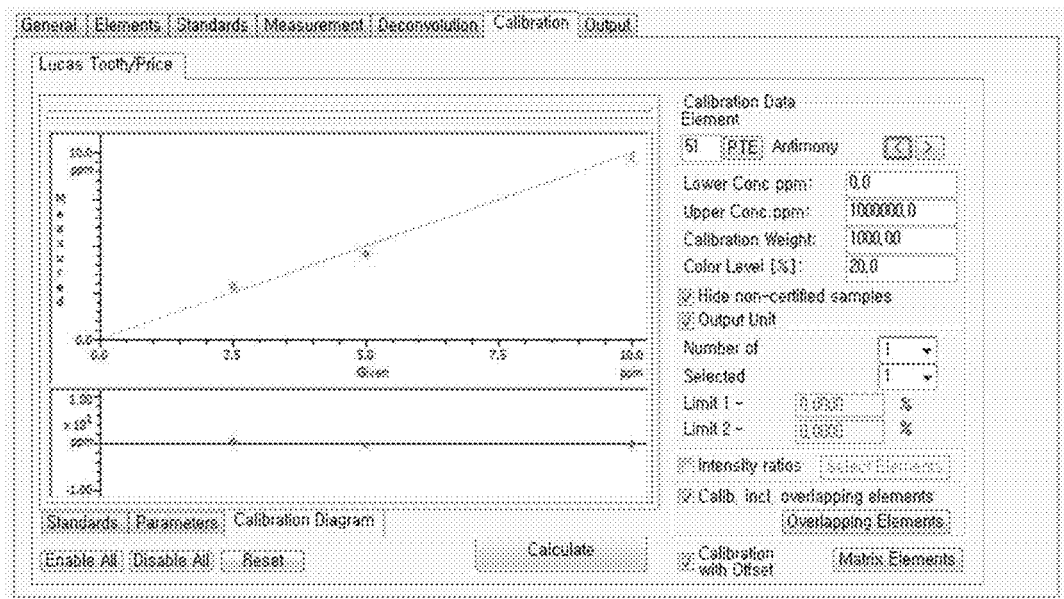
[Figure 6]
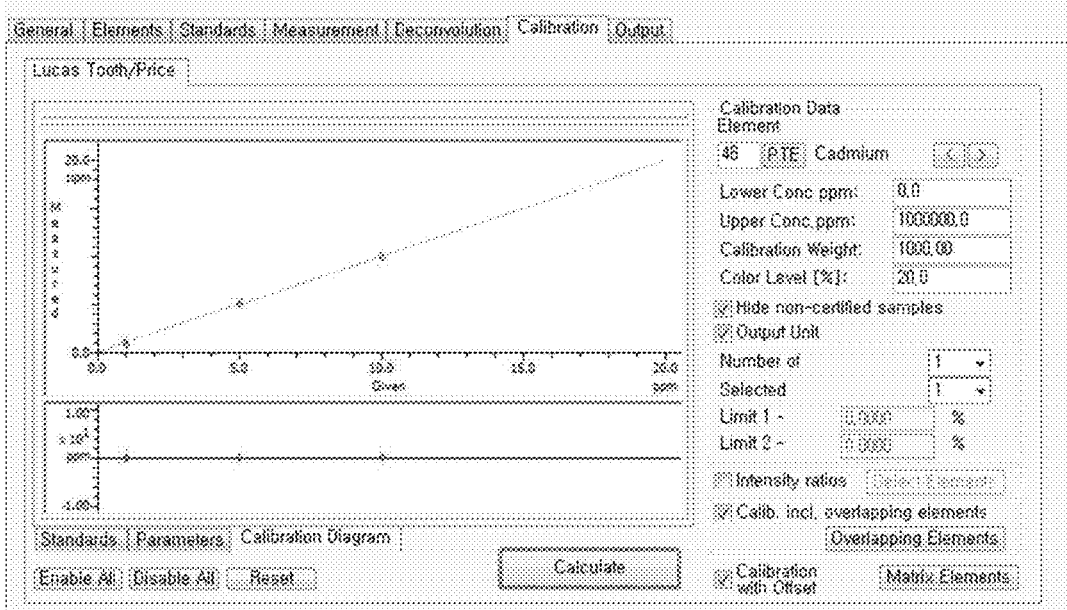

[Figure 7]
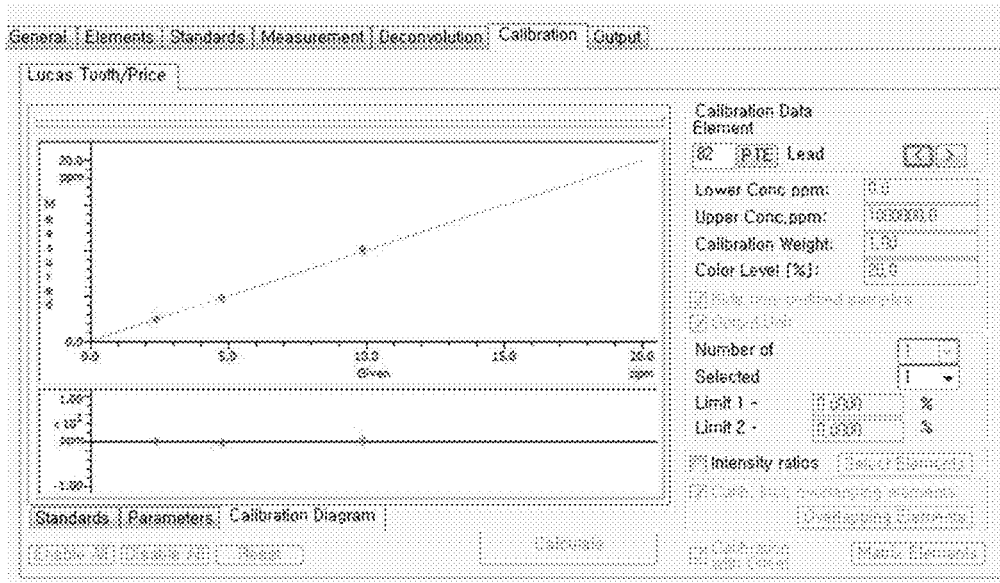
[Figure 8]
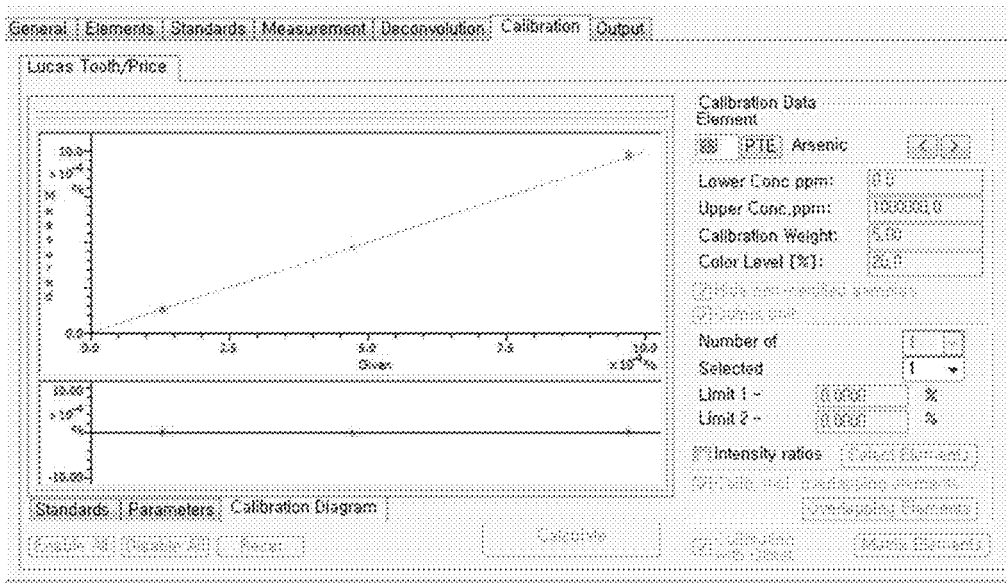

[Figure 9]
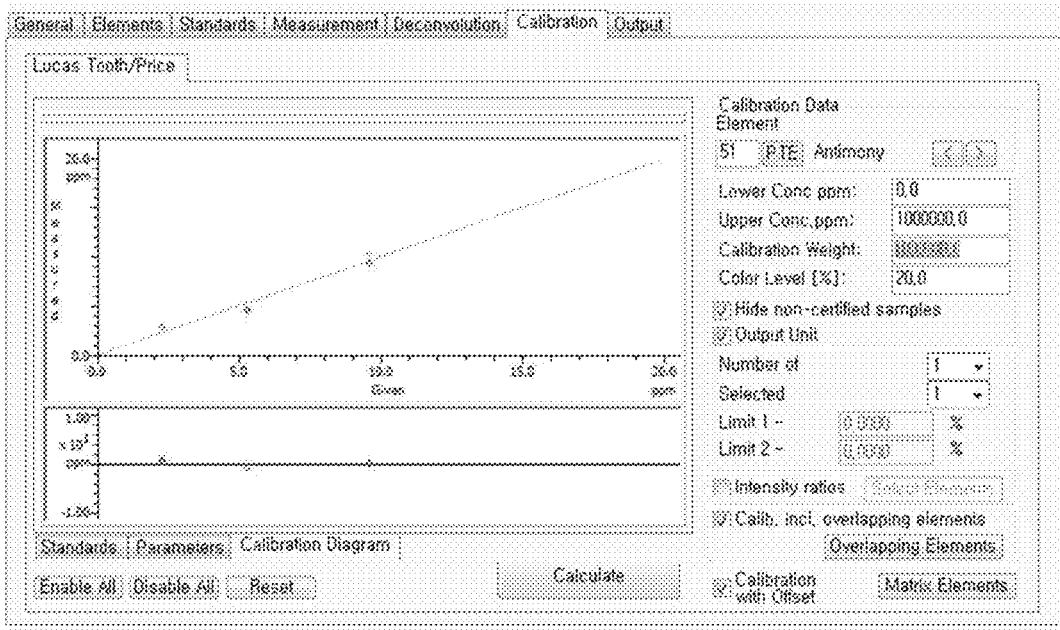
[Figure 10]
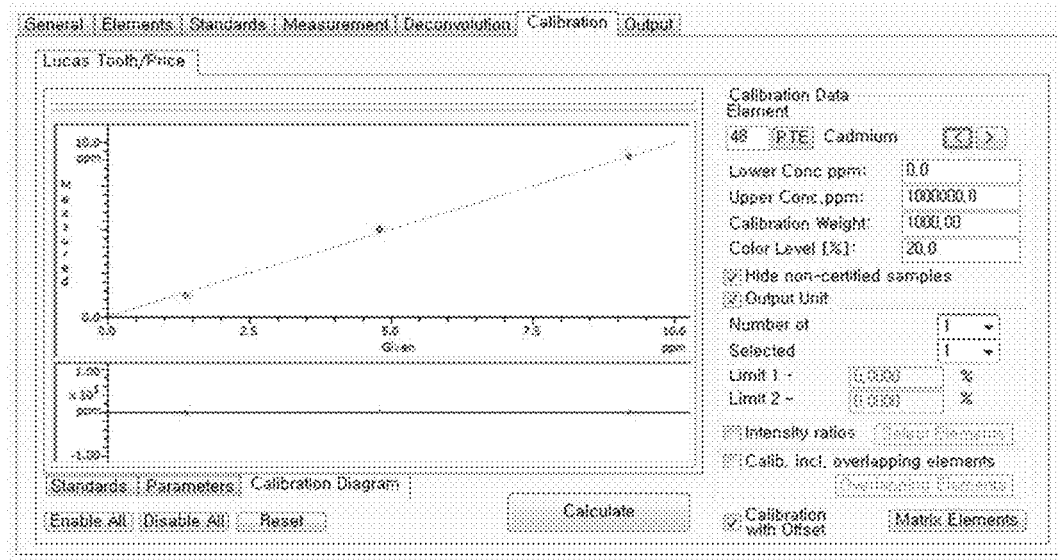

METHOD FOR QUANTITATIVE ANALYSIS OF HEAVY METALS

TECHNICAL FIELD

The present invention relates to a method for quantitative analysis of heavy metals, particularly lead, arsenic, antimony or cadmium.

This application claims the benefit of the filing dates of Korean Patent Application Nos. 10-2014-0152128, 10-2014-0152129, 10-2014-0152130 and 10-2014-0152131, all filed on Nov. 4, 2014, the content of which is incorporated herein by reference in its entirety.

BACKGROUND ART

In recent years, it has been reported that the strong toxicity of heavy metal-containing compounds and the accumulation of these heavy metals in the internal organs cause various fatal diseases. For this reason, the use of heavy metals has been strictly restricted.

Trace heavy metals contained in cosmetic products are those released from raw materials used for the production of the cosmetic products, and are problematic when they are present in trace amounts that do not harm human health. However, if cosmetic products contain excessive amounts of heavy metals such as lead, arsenic, antimony, cadmium, mercury, cobalt and nickel, these heavy metals can cause serious diseases such as skin diseases.

The allowable contents of lead, arsenic, mercury, antimony and cadmium in cosmetic products have been restricted, but there are no particular restrictions on other heavy metals. However, the incidence of allergy by heavy metals such as nickel and cobalt has gradually increased, and thus the use of these heavy metals has been gradually limited.

Magnesium, copper, iron and zinc were approved for use in cosmetic products, because they ensure safety for human use depending on their oxidation state or molecular structure. However, the use of such heavy metals in orally inhalable products has been restricted.

Due to the reports of studies on allergy caused by heavy metals and heavy metal toxicity as described above, consumers demand safer products, and thus there is an urgent needed to ensure the safety of cosmetic products against heavy metals.

However, as is known in the analysis field, it is difficult to analyze heavy metals dissolved in complex matrices such as cosmetic products. Analysis instruments that have conventionally been used include atomic absorption spectrometers (AAS) and inductively coupled plasma (ICP) analyzers. However, methods employing these analysis instruments require a long pretreatment time and use strong acids such as hydrofluoric acid, and for this reason, these methods are unsuitable for use in the quality control of raw materials and products, and thus the use thereof is limited.

Patents related to the X-ray fluorescence (XRF) analysis of heavy metals have already been reported. However, these patents mention neither technology relating to the preparation of standard samples nor technology relating to matrix correction methods. Thus, when the technologies disclosed in these patents were applied to complex matrices containing organic materials and various inorganic metals, such as cosmetic products, accurate analysis was difficult and trace quantitative analysis was impossible, due to errors caused by matrix differences and measurement errors caused by interference.

DISCLOSURE

Technical Problem

Accordingly, the present inventors have developed a method of pretreating a cosmetic sample for analysis so as to have a matrix similar to a standard sample, and as a result, have developed a simple and convenient quantitative analysis method capable of accurately analyzing trace heavy metals such as lead, arsenic, antimony or cadmium, which are present in various types of samples, by an X-ray fluorescence analysis method, thereby completing the present invention.

Therefore, it is an object of the present invention to provide an optimal X-ray fluorescence analysis method capable of analyzing tract lead, arsenic, antimony or cadmium, which is present in a liquid sample, in a simple, convenient, quick and accurate manner.

Technical Solution

In accordance with a first aspect of the present invention, there is provided a method for quantitative analysis of heavy metals, the method comprising:

a step of preparing a nitric acid solution that is a blank liquid standard sample;

a step of preparing two or more liquid standard samples having different concentrations by adding lead, arsenic, antimony or cadmium to the nitric acid solution;

a step of selecting an interfering element, which has an energy level overlapping with that of an X-ray spectrum detected by irradiating X-rays to lead, arsenic, antimony or cadmium, from among elements detected by irradiating X-rays to an analytical sample;

a deconvolution step of correcting the detected energy peak of lead, arsenic, antimony or cadmium, among energy peaks detected by irradiating X-rays to the liquid standard samples having different concentrations in the step of selecting the interfering element, from a detected energy peak of the overlapping interfering element;

a step of irradiating X-rays to each of the prepared liquid standard samples having different concentrations, and then performing the deconvolution step, thereby preparing a standard calibration curve; and a step of irradiating X-rays to the analytical sample to detect an energy peak, and then measuring the concentration of lead, arsenic, antimony or cadmium in the analytical sample based on the detected energy peak value of the analytical sample by the prepared standard calibration curve according to a standard calibration method.

In accordance with a second aspect of the present invention, there is provided a method for quantitative analysis of heavy metals, the method comprising:

a step of preparing talc powder as a blank powdery standard sample;

a step of preparing two or more powdery standard samples having different concentrations by adding lead, arsenic, antimony or cadmium to the talc powder;

a step of selecting an interfering element, which has an energy level overlapping with that of an X-ray spectrum detected by irradiating X-rays to lead, arsenic, antimony or cadmium, from among elements detected by irradiating X-rays to an analytical sample;

a deconvolution step of correcting the detected energy peak of lead, arsenic, antimony or cadmium, among energy peaks detected by irradiating X-rays to the powdery standard samples having different concentrations in the step of selecting the interfering element, from a detected energy peak of the overlapping interfering element;

a step of irradiating X-rays to each of the prepared powdery standard samples having different concentrations, and then performing the deconvolution step, thereby preparing a standard calibration curve; and a step of irradiating X-rays to the analytical sample to detect an energy peak, and then measuring the concentration of lead, arsenic, antimony or cadmium in the analytical sample based on the detected energy peak value of the analytical sample by the prepared standard calibration curve according to a standard calibration method.

Advantageous Effects

The method for quantitative analysis of heavy metals according to the present invention requires no pretreatment of sample, and thus can achieve analysis in a simple, convenient and quick manner. Furthermore, the analysis method according to the present invention can accurately analyze trace heave metals through preparation of a calibration curve based on prepared standard samples, selection of the optimum target, and elimination of the effect of an interfering element. In addition, the analysis method according to the present invention can simultaneously analyze lead, arsenic, antimony and cadmium in a sample, even if the amount of the sample is trace or the formulation of the sample is liquid or powder. Thus, the analysis method according to the present invention can effectively and quantitatively analyze lead, arsenic, antimony and cadmium, which should not be contained in foods and cosmetic products. Accordingly, the method according to the present invention can be effectively used for quality evaluation of foods and cosmetic products to provide better quality products to consumers.

DESCRIPTION OF DRAWINGS

FIG. 3 shows a standard calibration curve for lead, prepared according to Example 2-1. The X-axis indicates the lead concentration (ppm) arithmetically calculated based on the amount of lead added to a lead standard sample, and the Y-axis indicates the concentration (ppm) of lead in the standard sample, calculated according to the step of correcting the absorption effect of an interfering element in the present invention.

FIG. 4 shows a standard calibration curve for arsenic, prepared according to Example 2-1. The X-axis indicates the arsenic concentration (ppm) arithmetically calculated based on the amount of arsenic added to an arsenic standard sample, and the Y-axis indicates the concentration (ppm) of arsenic in the standard sample, calculated according to the step of correcting the absorption effect of an interfering element in the present invention.

FIG. 5 shows a standard calibration curve for antimony, prepared according to Example 2-2. The X-axis indicates the antimony concentration (ppm) arithmetically calculated based on the amount of antimony added to an antimony standard sample, and the Y-axis indicates the concentration (ppm) of antimony in the standard sample, calculated according to the step of correcting the absorption effect of an interfering element in the present invention.

FIG. 6 shows a standard calibration curve for cadmium, prepared according to Example 2-2. The X-axis indicates the cadmium concentration (ppm) arithmetically calculated based on the amount of cadmium added to a cadmium standard sample, and the Y-axis indicates the concentration (ppm) of lead in the standard sample, calculated according to the step of correcting the absorption effect of an interfering element in the present invention.

FIG. 7 shows a standard calibration curve for lead, prepared according to Example 2-3. The X-axis indicates the lead concentration (ppm) arithmetically calculated based on the amount of lead added to a lead standard sample, and the Y-axis indicates the concentration (ppm) of lead in the standard sample, calculated according to the step of correcting the absorption effect of an interfering element in the present invention.

FIG. 8 shows a standard calibration curve for arsenic, prepared according to Example 2-3. The X-axis indicates the arsenic concentration (ppm) arithmetically calculated based on the amount of arsenic added to an arsenic standard sample, and the Y-axis indicates the concentration (ppm) of arsenic in the standard sample, calculated according to the step of correcting the absorption effect of an interfering element in the present invention.

FIG. 9 shows a standard calibration curve for antimony, prepared according to Example 2-4. The X-axis indicates the antimony concentration (ppm) arithmetically calculated based on the amount of antimony added to an antimony standard sample, and the Y-axis indicates the concentration (ppm) of antimony in the standard sample, calculated according to the step of correcting the absorption effect of an interfering element in the present invention.

FIG. 10 shows a standard calibration curve for cadmium, prepared according to Example 2-4. The X-axis indicates the cadmium concentration (ppm) arithmetically calculated based on the amount of cadmium added to a cadmium standard sample, and the Y-axis indicates the concentration (ppm) of lead in the standard sample, calculated according to the step of correcting the absorption effect of an interfering element in the present invention.

MODE FOR INVENTION

Figure 1:
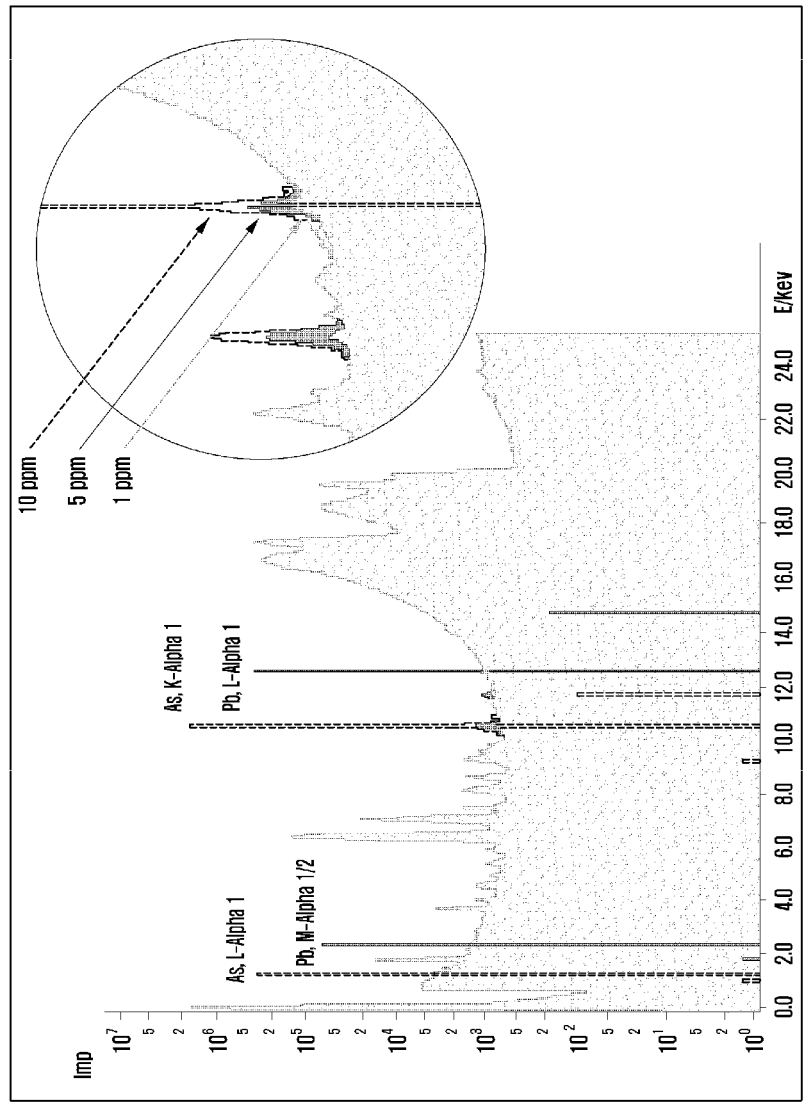
FIG. 1 shows X-ray spectra measured by irradiating X-rays to liquid standard samples having different concentrations of lead and arsenic according to Example 2-1. The X-axis of the spectrum indicates energy level (keV), and the Y-axis indicates energy intensity. The L-alpha energy level of lead is 10.550 keV, and the K-alpha energy level of arsenic is 10.542 keV.
Figure 2:
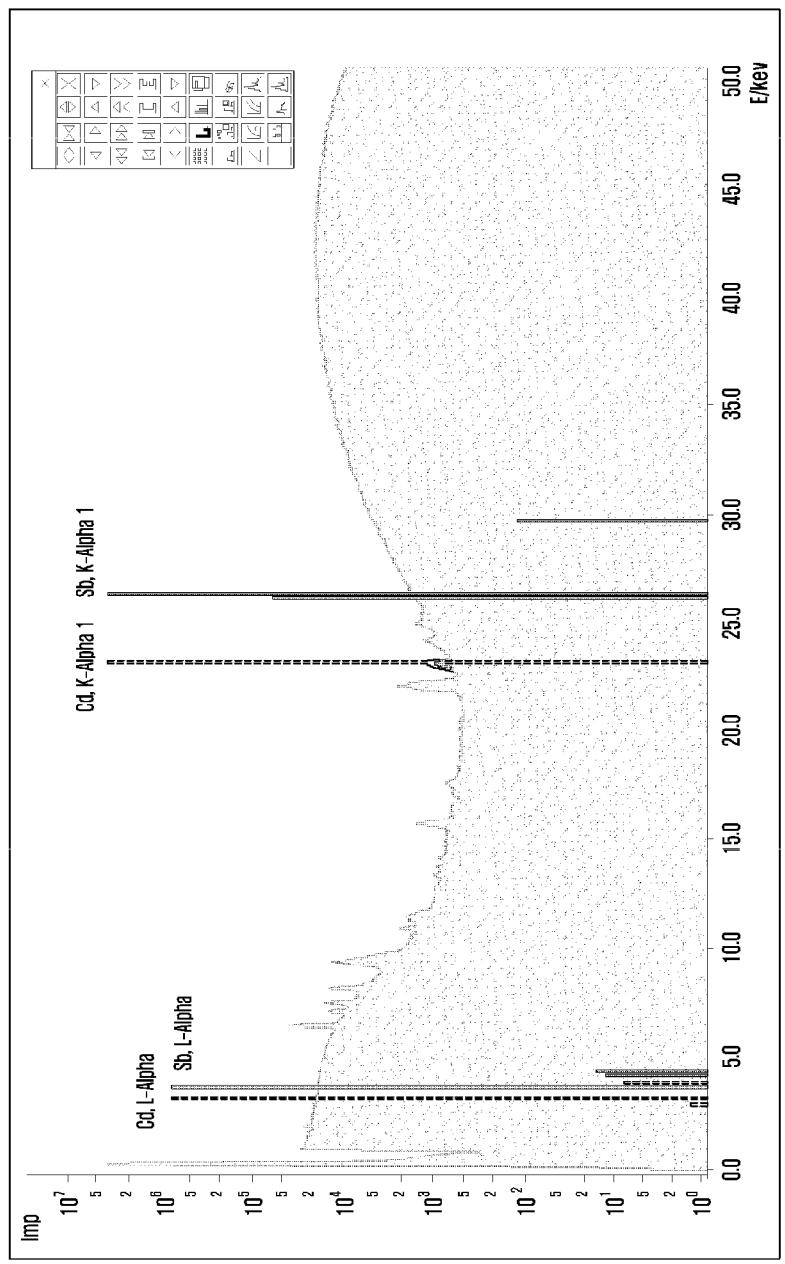
FIG. 2 shows X-ray spectra measured by irradiating X-rays to liquid standard samples having different concentrations of antimony and cadmium according to Example 2-2. The X-axis of 20 the spectrum indicates energy level (keV), and the Y-axis indicates energy intensity. The K-alpha energy level of antimony is 26.355 keV, and the K-alpha energy level of cadmium is 23.170 keV.

As used herein, the term "lead" means a post-transition metal element of group 14 of the periodic table, which has an atomic symbol of Pb and an atomic number of 82.

As used herein, the term "arsenic" means a semi-metal element of group 15 of the periodic table, which has an atomic symbol of As and an atomic number of 33.

As used herein, the term "antimony" means a semi-metal element of group 15 of the periodic table, which has an atomic symbol of Sb and an atomic number of 51.

As used herein, the term "cadmium" means a transition metal element of group 12 of the periodic table, which has an atomic symbol of Cd and an atomic number of 48.

All the steps of the method for quantitative analysis of heavy metals according to the present invention may be selectively and independently performed with respect to any one heavy metal among lead, arsenic, antimony and cadmium. For example, during quantitative analysis of lead, the step regarding arsenic, antimony and cadmium may not be performed, and during quantitative analysis of arsenic, the step regarding lead, antimony and cadmium may not be performed, and during quantitative analysis of antimony, the step regarding lead, arsenic and cadmium may not be performed, and during quantitative analysis of cadmium, the step regarding lead, arsenic and antimony may not be performed.

As used herein, the term "analytical sample" means a certain amount of a sample taken from the material to be analyzed in order to measure the concentration of lead, arsenic, antimony or cadmium in the material to be analyzed.

As used herein, the term "blank sample" means a sample that does not contain lead, arsenic, antimony or cadmium.

As used herein, the term "standard sample" means a sample obtained by adding a fixed amount of lead, arsenic, antimony or cadmium to a blank sample so as to enable the concentration of lead, arsenic, antimony or cadmium to be arithmetically calculated.

As used herein, the term "standard samples having different concentrations" means two or more standard samples having different concentrations of lead, arsenic, antimony or cadmium.

As used herein, the term "energy peak" means an energy intensity value corresponding to the energy level of an X-ray spectrum which is detected when X-rays are irradiated to a sample.

As used herein, "standard calibration curve" means a two-dimensional relationship between a concentration value, arithmetically calculated on standard samples having different concentrations, and an energy peak intensity value corresponding to the energy level of lead, arsenic, antimony or cadmium, detected by irradiating X-rays. The standard calibration curve can be determined by a linear or curve approximation.

According to an embodiment of the present invention, the deconvolution step further comprises a step of correcting the absorption effect of an interfering element to remove an energy intensity value corresponding to an energy level range in which the detected energy peak of lead, arsenic, antimony or cadmium overlaps with the energy peak of a selected interfering element.

The step of correcting the absorption effect of the interfering element comprises correcting a matrix effect in which an energy value measured by irradiating X-rays to a sample is changed due to elements other than lead, arsenic, antimony or cadmium to affect the measurement of concentration of lead, arsenic, antimony or cadmium in the sample, so that the analysis method of the present invention can accurately measure the concentration of lead, arsenic, antimony or cadmium in the sample.

According to an embodiment of the present invention, the step of correcting the absorption effect of the interfering element further comprises a step of correcting the detected energy peak of lead, arsenic, antimony or cadmium by the Lucas-Tooth/Price algorithm.

According to an embodiment of the present invention, the step of correcting the detected energy peak of lead, arsenic, antimony or cadmium by the Lucas-Tooth/Price algorithm further comprises a step of collecting the detected energy peak of lead, arsenic, antimony or cadmium by the following Equation 1:

$$W_i = B_i + I_i \left[ k_i + \sum_j a_{ij} I_j \right] \quad \text{Equation 1}$$

wherein i is any one element of lead, arsenic, antimony and cadmium; j is an element interfering with i; $W_i$ is the mass-based concentration of lead, arsenic, antimony or cadmium in a sample; $I_i$ is the energy peak intensity of lead, arsenic, antimony or cadmium; $I_j$ is the energy peak intensity of elements other than lead, arsenic, antimony or cadmium; $k_i$ is the proportional constant of the mass-based concentration to the detected energy intensity of lead, arsenic, antimony or cadmium; $a_{ij}$ is the correction constant of the absorption effect of the detected energy peak of the interfering element for the detected energy peak of lead, arsenic, antimony or cadmium; and $B_i$ is a background constant corresponding to when the concentration of lead, arsenic, antimony or cadmium concentration is 0.

According to an embodiment of the present invention, $B_i$, $K_i$ and $a_{ij}$ in Equation 1 are used to determine the detected energy peak values of two or more liquid standard samples having different concentrations by the linear-squares method.

In the present invention, the nitric acid solution that is used as the blank liquid standard sample contains neither the lead, arsenic, antimony or cadmium to be analyzed, nor an element having an energy level near the energy level of each of lead, arsenic, antimony and cadmium, and thus causes no interference during quantitative analysis of lead, arsenic, antimony or cadmium in a sample. Thus, the nitric acid solution is suitable as a blank sample.

According to an embodiment of the present invention, the concentration of the nitric acid solution that is used in the step of preparing the liquid standard sample and the step of preparing the liquid standard samples having different concentrations is 5-10%. If the concentration of the nitric acid solution is lower than 5%, lead, arsenic, antimony or cadmium cannot be dissolved therein, and if the concentration of the nitric acid solution is higher than 10%, the nitric acid solution can dissolve either the material of a container for the sample or a film coated on the container surface.

In the present invention, talc powder that is used as the blank liquid standard sample contains neither the lead, arsenic, antimony or cadmium to be analyzed, nor an element having an energy level near the energy level of each of lead and arsenic, and thus causes no interference during quantitative analysis of lead or arsenic in a sample. Thus, the talc powder is suitable as a blank sample.

According to an embodiment of the present invention, detection of the energy peak in the deconvolution step and the step of measuring the concentration of lead, arsenic, antimony or cadmium in the sample is performed by an X-ray fluorescence analysis method.

According to an embodiment of the present invention, the X-rays that are used in the deconvolution step and the step of measuring the concentration of lead, arsenic, antimony or cadmium in the sample are irradiated to the analytical sample or the standard sample through a polarizing plate comprising any one or more selected from the group consisting of molybdenum, aluminum, aluminum oxide, palladium, titanium, zirconium and cobalt. The background can be corrected using an energy peak value corresponding to the material of the polarizing plate, and when the polarizing plate comprises molybdenum, the X-ray spectrum measured will have high sensitivity.

According to an embodiment of the present invention, the method for quantitative analysis of heavy metals is a method for quantitative analysis of lead, and the interfering element is any one or more selected from the group consisting of thallium, arsenic, bismuth and polonium.

According to an embodiment of the present invention, in the method for quantitative analysis of lead, the interfering element thallium has a peak L-alpha energy level of 10.267 keV; the interfering element arsenic has a peak K-alpha energy level of 10.542 keV; the interfering element bismuth has a peak L-alpha energy level of 10.837 keV; and the interfering element polonium has a peak L-alpha energy level of 11.129 keV.

According to an embodiment of the present invention, the method for quantitative analysis of heavy metals is a method for quantitative analysis of arsenic, and the interfering element is any one or more selected from the group consisting of gallium, germanium, lead and selenium.

According to an embodiment of the present invention, in the method for quantitative analysis of arsenic, the interfering element gallium has a peak K-alpha energy level of 9.250 keV; the interfering element germanium has a peak K-alpha energy level of 9.885 keV; the interfering element lead has a peak L-alpha energy level of 10.550 keV; and the interfering element selenium has a peak K-alpha energy level of 11.220 keV.

According to an embodiment of the present invention, the method for quantitative analysis of heavy metals is a method for quantitative analysis of antimony, and the interfering element is any one or more selected from the group consisting of tin, tellurium and iodine.

According to an embodiment of the present invention, in the method for quantitative analysis of antimony, the interfering element thallium has a peak K-alpha energy level of 25.267 keV; the interfering element tellurium has a peak K-alpha energy level of 27.468 keV; and the interfering element iodine has a peak K-alpha energy level of 28.607 keV.

According to an embodiment of the present invention, the method for quantitative analysis of heavy metals is a method for quantitative analysis of cadmium, and the interfering element is any one or more selected from the group consisting of silver, indium and tin.

According to an embodiment of the present invention, in the method for quantitative analysis of cadmium, the interfering element silver has a peak K-alpha energy level of 22.159 keV; the interfering element indium has a peak K-alpha energy level of 24.206 keV; and the interfering element tin has a peak K-alpha energy level of 25.267 keV.

According to an embodiment of the second aspect of the present invention, the method for quantitative analysis of heavy metals is a method for quantitative analysis of lead, and lead in the step of preparing the standard samples having different concentrations is an oxide of lead.

Specifically, the oxide of lead may be lead monoxide (PbO).

According to an embodiment of the second aspect of the present invention, the method for quantitative analysis of heavy metals is a method for quantitative analysis of arsenic, and arsenic in the step of preparing the standard samples having different concentrations is an oxide of arsenic.

Specifically, the oxide of arsenic may be arsenic trioxide ($As_2O_3$).

According to an embodiment of the present invention, the analytical sample is a cosmetic composition or a food composition.

According to an embodiment of the first aspect of the present invention, the cosmetic composition may be a lotion, ointment, gel or cream formulation, and is not specifically limited, as long as it is in a liquid form.

According to an embodiment of the first aspect of the present invention, the food composition may be a beverage, and is not specifically limited, as long as it is in a liquid form.

According to an embodiment of the second aspect of the present invention, the cosmetic composition may be a composition contained in eye shadow, nail lacquer or mud pack, and is not specifically limited, as long as it is in a powder form.

According to an embodiment of the second aspect of the present invention, the food composition is specifically limited, as long as it is in a powder form.

According to an embodiment of the present invention, the step of measuring the concentration of lead, arsenic, antimony or cadmium in the analytical sample is performed without pretreatment of the analytical sample.

According to an embodiment of the present invention, the correlation coefficient of the prepared standard calibration curve is 0.99 or more.

Hereinafter, the present invention will be described in further detail with reference to examples. It is to be understood, however, that these examples for illustrative purposes only and are not intended to limit the scope of the present invention.

Example 1-1: Selection of Optimum Conditions for Liquid Sample Analysis

In order to highly accurately analyze the lead, arsenic, antimony or cadmium contained in the sample to be analyzed, the following experiments were performed to determine the optimum conditions.

1-1. Selection of Analysis Method

Methods for analysis of heavy metal contents include wet analysis methods, atomic absorption spectrometry methods and inductively coupled plasma spectrometry methods. These analysis methods are performed by treating a sample with acid to make a solution and quantifying each element in the sample solution. However, these analysis methods have shortcomings in that a process for pretreatment of the sample to be analyzed is complex, the pretreatment time is 5 hours or more, and a highly toxic acid is used, which poses a health risk to the operators. In addition, the wet analysis methods or the atomic absorption spectrometry methods cannot perform simultaneous analysis and also have low accuracy. Thus, these analysis methods are unsuitable for use in quality control.

For these reasons, the present inventors adopted an X-ray fluorescence analysis method which requires a simple pretreatment method, uses no toxic strong acid, has a short analysis time, and has ensured accuracy.

1-2. Selection of Blank Sample

In order to prepare a liquid standard sample at a suitable concentration, nitric acid, sulfuric acid, phosphoric acid or the like for use as a blank solution for dilution was tested at various concentrations.

It is required that a blank sample does not contain lead, arsenic, antimony or cadmium and that other elements are not detected in the blank sample at positions similar to an energy level at which lead, arsenic, antimony or cadmium is detected. The blank sample for liquid sample measurement, which satisfies such requirements, should be able to dissolve a certain amount of lead, arsenic, antimony or cadmium. For XRF analysis, a 5-100 nitric acid solution that does not dissolve the film of a sample cup was used.

2-1. Elimination of Effect of Peak Overlap—Deconvolution

An X-ray fluorescence analyzer can separate elements according to their characteristic energy values, and is based on the principle according to which the pulse height of a detector signal is proportional to X-ray photon energy having a correlation with wavelength. Based on this principle, the X-ray fluorescence analyzer can quantify each element from the pulse of an energy level according to the concentration of the element.

When a sample containing heavy metals is exposed to X-rays, an electron in the K shell of each element is emitted, and an electron in the L shell moves to the K shell for orbital stabilization. At this time, characteristic X-rays corresponding to the difference in energy level between the two shells are generated, and thus each of the elements can be quantified from the characteristic energy values of the K shell, L shell, M shell . . . of each element.

However, if the matrix of the sample is complex, the overlapping of X-ray peaks will occur, thus reducing the accuracy of analysis.

Technology for eliminating the effect of such X-ray overlapping is deconvolution. Single elements have various energy values, including $K_\alpha$, $K_\beta$, $K_\gamma$, $L_\alpha$, $L_\beta$, $L_\gamma$, $M_\alpha$, $M_\beta$, $M_\gamma$, etc. The ratio of these energy intensities is constant. In other words, when the $K_\alpha$ energy intensity is 10, $K_\beta$ is 6, $K_\gamma$ is 2, and $L_\alpha$ is 4, indicating that each element has characteristic energy intensity values.

If the $K_\alpha$ of Ti overlaps with the $K_\alpha$ of V, the $K_\beta$ or $L_\alpha$ cannot overlap. In this case, when the $K_\alpha$ energy value of V is removed from the overlapping $K_\alpha$ of Ti by deconvolution after calculating the energy intensity of V with the $K_\beta$ or $L_\alpha$ energy level, the energy value of only Ti can be obtained, and thus the matrix effect can be corrected.

2-2. Selection of Interfering Elements

To select potential interfering elements in order to apply the deconvolution described in Example 2-1, all elements contained in samples having a complex matrix were scanned. The energy range of lead, arsenic, antimony or cadmium to be analyzed was determined to select elements having high interference potential.

2-3. Optimum Conditions for Analysis (Analysis of Lead or Arsenic)

After setting the conditions as described above, lead and arsenic in the samples to be analyzed were analyzed using an X-ray fluorescence analyzer. Standard samples of lead and arsenic and analytical samples were used for correction of backgrounds with molybdenum crystal, and interfering elements were selected in order to eliminate the effect of a matrix. Lead and arsenic contained in samples were measured using the Lucas-Tooth model with deconvolution for 1000 seconds per sample. In the following Examples of the present invention, the analysis of lead or arsenic was performed under the conditions shown in Table 1 below.

TABLE 1

| | |
|---|---|
| X-ray voltage | 60 W |
| Polarizing crystal | Molybdenum |
| Detector | SDD silicon drift detector (Spectral resolution (FWHM) at Mn K-alpha ≤160 eV) |
| Measurement time | 1000 seconds |
| Correction model | Lucas-Tooth/Price Model |

2-4. Optimum Conditions for Analysis (Analysis of Antimony or Cadmium)

After setting the conditions as described above, lead and arsenic in the samples to be analyzed were analyzed using an X-ray fluorescence analyzer. Standard samples of antimony and cadmium and analytical samples were used for correction of backgrounds with molybdenum crystal, and interfering elements were selected in order to eliminate the effect of a matrix. Antimony and cadmium contained in samples were measured using the Lucas-Tooth model with deconvolution for 1000 seconds per sample. In the following Examples of the present invention, the analysis of antimony or cadmium was performed under the conditions shown in Table 2 below.

TABLE 2

| | |
|---|---|
| X-ray voltage | 60 W |
| Polarizing crystal | Aluminum oxide |
| Detector | SDD silicon drift detector (Spectral resolution (FWHM) at Mn K-alpha ≤160 eV) |
| Measurement time | 1000 seconds |
| Correction model | Lucas-Tooth/Price Model |

Example 2-1: Analysis of Lead and Arsenic in Liquid Sample

Using the optimum conditions selected in Example 1-1, the following experiments were performed in order to actually analyze lead present in various samples.

3-1. Analysis Instrument (XRF)

The X-ray fluorescence analyzer used in this Example was Xepos HE (Specto), and data processing was performed using X-Lap Pro program (Specto).

3-2. Standard Samples

As lead (INCI name: lead; atomic symbol: Pb) used in a liquid standard sample, lead manufactured by Sigma was used as a concentration of 1000 ppm, and as arsenic (INCI name: arsenic; atomic symbol: As) used in a liquid standard sample, arsenic manufactured by Sigma was used as a concentration of 1000 ppm.

3-3. Quantitative Analysis of Lead and Arsenic in Liquid Cosmetic Raw Materials

On liquid cosmetic raw materials, a method for quantitative analysis of lead and arsenic according to an embodiment of the present invention was performed.

First, about 6 mL of liquid cosmetic raw material 1 placed in a sample cup without bubbles was used as an analytical sample. In addition, 0.1 mL, 0.5 mL and 1 mL of the above-described lead standard sample were placed in 100 mL flasks, and then dispersed with 5-10% nitric acid solution according to marked lines, thereby preparing standard samples having different concentrations of 1 ppm, 5 ppm and 10 ppm. Energy peaks were measured on the analytical sample and the standard samples by an X-ray fluorescence analyzer under the following conditions, and based on the measured energy peaks, a standard calibration curve was determined using the linear squares method of Equation 1. According to a standard calibration method using the determined standard calibration curve, the concentration of lead in the analytical sample was analyzed. This procedure was also performed on liquid cosmetic raw materials 2 to 6 in the same manner.

In addition, the concentration of arsenic was analyzed in the same manner as the analysis of lead, except that a standard arsenic sample was used instead of the lead standard sample.

Figure 11:
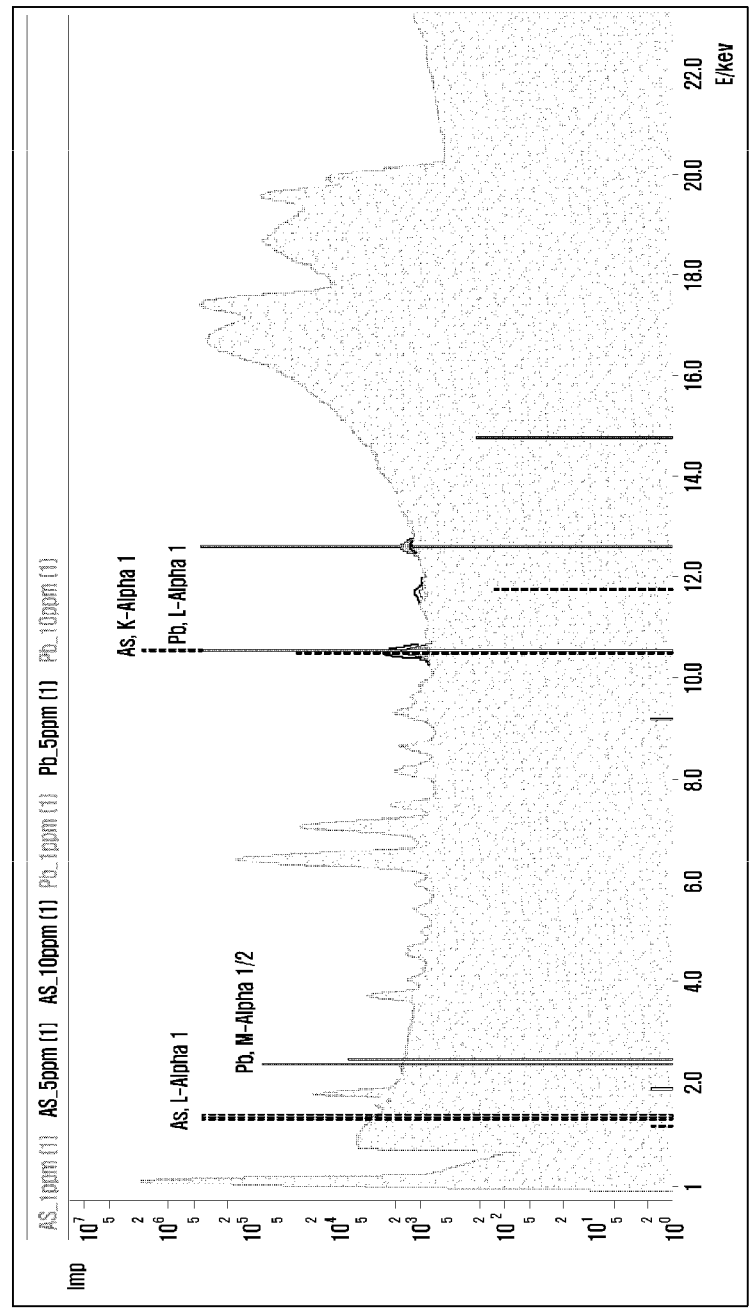
FIG. 11 shows X-ray spectra obtained by correcting values, measured by irradiating X-rays to liquid cosmetic raw materials, according to the step of correcting the absorption effect of an interfering element, in Example 2-1. The X-axis of the spectrum indicates energy level (keV), and the Y-axis indicates energy intensity.

The spectra of liquid cosmetic raw materials 1 to 5, which resulted from the analysis, are shown in FIG. 11, and the results of measuring the concentrations of lead and arsenic in liquid cosmetic raw materials 1 to 5 are shown in Table 3 below.

TABLE 3

| Sample | Concentration (ppm) | |
| --- | --- | --- |
| | Lead | Arsenic |
| Liquid cosmetic raw material 1 (trade name: Solaveil CT100, manufactured by Croda) | 1.3 | 0 |
| Liquid cosmetic raw material 2 (trade name: VEGFTa Red, manufactured by Gattefosse) | 2.2 | 0.8 |
| Liquid cosmetic raw material 3 (trade name: VE2ETOL, manufactured by Bioland) | 0 | 0 |
| Liquid cosmetic raw material 4 (trade name: Dekanex2008FG, manufactured by IMCD) | 0 | 0.6 |
| Liquid cosmetic raw material 5 (trade name: Hydra cires, manufactured by Gattefosse) | 0.9 | 0 |

The standard calibration curves used to quantify the analyzed arsenic and lead were prepared in the range of 1.0-10 ppm. As can be seen in FIGS. 3 and 4, the prepared standard calibration curves had a correlation coefficient (R) of 0.999 or more, indicating that they had good linearity.

4-1. Comparative Example: Quantitative Analysis of Lead and Arsenic in Liquid Cosmetic Raw Material by ICP-MS (1) Preparation of analytical sample solution: 0.2 g of liquid cosmetic raw material 1 as an analytical sample was placed in a vessel made of Teflon so as not to come into contact with the wall of the vessel. To decompose the analytical sample, 7 mL of nitric acid and 2 mL of hydrofluoric acid were placed in the vessel which was then covered with a lid and mounted in a microwave oven, and the analytical sample was decomposed under the following operating conditions 1 until it became colorless or yellow. The vessel was cooled to room temperature, and then the lid was opened. 20 mL of diluted (5-100) boric acid was placed in the vessel which was then covered with the lid mounted in the microwave oven, and fluorine was inactivated under the following operating conditions 2. The vessel was cooled to room temperature, and then the lid was carefully opened, and the decomposed material was transferred into a 100 mL flask. The vessel and the lid were washed with a suitable amount of distilled water, and distilled water was added to the decomposed material to a volume of 100 mL. If a precipitate existed, it was used after filtration. The resulting material was diluted 5-fold with distilled water, thereby preparing an analytical sample solution. In addition, a blank sample was prepared using 7 mL of nitric acid and 2 mL in the same manner as the preparation of the analytical sample solution.

TABLE 4

| Operating conditions 1 | Operating conditions 2 |
| --- | --- |
| Maximum power: 1000 W | Maximum power: 1000 W |
| Peak temperature: 200 | Peak temperature: 180 |
| Decomposition temperature: about 20 min | Decomposition temperature: about 10 min |

(2) Preparation of standard sample solutions: Diluted (2→100) nitric acid was added to a lead standard solution (1000 μg/mL), thereby preparing three or more calibration standard sample solutions having different concentrations. The calibration standard sample solutions contained 1-20 ng of lead per mL of solution.

(3) Analysis operation: According to the following operating conditions 3, each of the standard solutions was analyzed by inductively coupled plasma mass spectrometry (ICP-MS) to obtain a calibration curve for lead, and the amount of lead in the analytical sample solution was measured using the obtained calibration curve.

<Operating Conditions 3>

Atomic weight: 206, 207 and 208 (selected and detected in a range in which there was no interference);

Plasma gas: argon (99.99 v/v % or more).

(4) The amount of lead in an analytical sample solution was measured in the same manner as described in steps (1) to (3) above, except that each of liquid cosmetic raw materials 2 to 5 was used instead of liquid cosmetic raw material 1.

(5) The amount of arsenic in an analytical sample solution was measured in the same manner as described in steps (1) to (4) above, except that arsenic was used instead of lead and that the following operating conditions 4 were used instead of operating conditions 3.

<Operating Conditions 4>

Wavelength: 193.759 nm (other characteristic wavelengths of arsenic may be selected if an interfering element is contained);

Plasma gas: argon (99.99 v/v % or more).

4-2. Comparison Between the Results of Quantitative Analysis According to Example of the Present Invention and the Results of Quantitative Analysis According to Comparative Example Table 5 below shows a comparison between the results of XRF analysis of lead and arsenic in the analytical samples (liquid cosmetic raw materials 1 to 5) according to the Example of the present invention and the results of ICP-MS analysis of lead and arsenic according to the Comparative Example.

TABLE 5

| | Content (ppm) | | | |
|---|---|---|---|---|
| | Lead | | Arsenic | |
| Sample | XRF | ICP-MS | XRF | ICP-MS |
| Liquid cosmetic raw material 1 | 1.3 | 1.5 | 0 | 0 |
| Liquid cosmetic raw material 2 | 2.2 | 1.8 | 0.8 | 1.0 |
| Liquid cosmetic raw material 3 | 0 | 0 | 0 | 0 |
| Liquid cosmetic raw material 4 | 0 | 0 | 0.6 | 0.3 |
| Liquid cosmetic raw material 5 | 0.9 | 0 | 0 | 0 |

From the results in Table 5 above, it was shown that, compared to the method for ICP-MS analysis of lead or arsenic, the method for analysis for lead or arsenic according to the Example of the present invention was simple and convenient, because there was no pretreatment of the analytical sample, and it could quickly provide results, because the analysis time was short. In addition, it was shown that the analysis method according to the Example of the present invention would be suitable for analysis of samples having various matrices, because it comprises the step of correcting the matrix effect. Furthermore, it was found that the ICP-MS analysis results and the analysis results according to the Example of the present invention all had a relative standard deviation of less than 1%, indicating that the analysis method of the present invention can achieve accurate analysis.

Example 2-2: Analysis of Antimony and Cadmium in Liquid Samples

Using the optimum conditions selected in Example 1-1, the following experiments were performed in order to actually analyze lead present in various samples.

3-1. Analysis Instrument (XRF)

The X-ray fluorescence analyzer used in this Example was Xepos HE (Specto), and data processing was performed using X-Lap Pro program (Specto).

3-2. Standard Samples

As antimony (INCI name: antimony; atomic symbol: Pb) used in a liquid standard sample, antimony manufactured by Sigma was used as a concentration of 1000 ppm, and as cadmium (INCI name: cadmium; atomic symbol: Cd) used in a liquid standard sample, cadmium manufactured by Sigma was used as a concentration of 1000 ppm.

3-3. Quantitative Analysis of Antimony and Cadmium in Liquid Cosmetic Raw Materials On liquid cosmetic raw materials, a method for quantitative analysis of antimony and cadmium according to an embodiment of the present invention was performed.

First, about 6 mL of liquid cosmetic raw material 1 placed in a sample cup without bubbles was used as an analytical sample. In addition, 0.1 mL, 0.5 mL and 1 mL of the above-described antimony standard sample were placed in 100 mL flasks, and then dispersed with 5-10% nitric acid solution according to marked lines, thereby preparing standard samples having different concentrations of 1 ppm, 5 ppm and 10 ppm. Energy peaks were measured on the analytical sample and the standard samples by an X-ray fluorescence analyzer under the following conditions, and based on the measured energy peaks, a standard calibration curve was determined using the linear squares method of Equation 1. According to a standard calibration method using the determined standard calibration curve, the concentration of antimony in the analytical sample was measured. This procedure was also performed on liquid cosmetic raw materials 2 to 6 in the same manner.

In addition, the concentration of cadmium was analyzed in the same manner as the analysis of antimony, except that a standard cadmium sample was used instead of the antimony standard sample.

Figure 12:
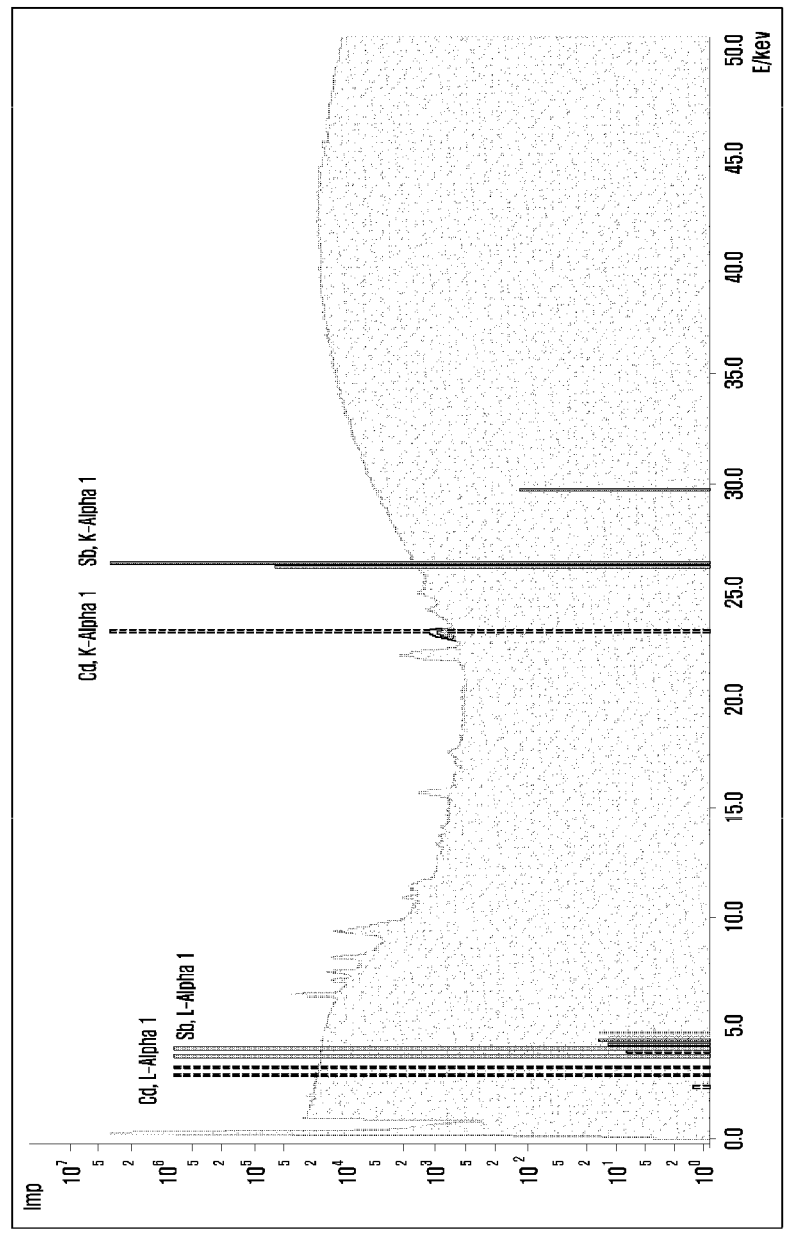
FIG. 12 shows X-ray spectra obtained by correcting values, measured by irradiating X-rays to liquid cosmetic raw materials, according to the step of correcting the absorption effect of an interfering element, in Example 2-2. The X-axis of the spectrum indicates energy level (keV), and the Y-axis indicates energy intensity.

The spectra of liquid cosmetic raw materials 1 to 5, which resulted from the analysis, are shown in FIG. 12, and the results of measuring the concentrations of antimony and cadmium in liquid cosmetic raw materials 1 to 5 are shown in Table 6 below.

TABLE 6

| | Concentration (ppm) | |
|---|---|---|
| Sample | Antimony | Cadmium |
| Liquid cosmetic raw material 1 (trade name: Solaveil CT100, manufactured by Croda) | 0 | 0 |
| Liquid cosmetic raw material 2 (trade name: VEGFTa Red, manufactured by Gattefosse) | 0 | 0.9 |
| Liquid cosmetic raw material 3 (trade name: VE2ETOL, manufactured by Bioland) | 0 | 0 |
| Liquid cosmetic raw material 4 (trade name: Dekanex2008FG, manufactured by IMCD) | 0 | 0 |
| Liquid cosmetic raw material 5 (trade name: Hydra cires, manufactured by Gattefosse) | 0 | 0.5 |

The standard calibration curves used to quantify the analyzed antimony and cadmium were prepared in the range of 1.0-10 ppm. As can be seen in FIGS. 5 and 6, the prepared standard calibration curves had a correlation coefficient (R) of 0.999 or more, indicating that they had good linearity.

4-1. Comparative Example: Quantitative Analysis of Antimony and Cadmium in Liquid Cosmetic Raw Material by ICP-MS (1) Preparation of analytical sample solution: 0.2 g of liquid cosmetic raw material 1 as an analytical sample was placed in a vessel made of Teflon so as not to come into contact with the wall of the vessel. To decompose the analytical sample, 7 mL of nitric acid and 2 mL of hydrofluoric acid were placed in the vessel which was then covered with a lid and mounted in a microwave oven, and the analytical sample was decomposed under the operating conditions 1 described in Example 2-1 above until it became colorless or yellow. The vessel was cooled to room temperature, and then the lid was opened. 20 mL of diluted (5-100) boric acid was placed in the vessel which was then covered with the lid mounted in the microwave oven, and fluorine was inactivated under the operating conditions 2 described in Example 2-1 above. The vessel was cooled to room temperature, and then the lid was carefully opened, and the decomposed material was transferred into a 100 mL flask. The vessel and the lid were washed with a suitable amount of distilled water, and distilled water was added to the decomposed material to a volume of 100 mL. If a precipitate existed, it was used after filtration. The resulting material was diluted 5-fold with distilled water, thereby preparing an analytical sample solution. In addition, a blank sample was prepared using 7 mL of nitric acid and 2 mL in the same manner as the preparation of the analytical sample solution.

(2) Preparation of standard sample solutions: Diluted (2→100) nitric acid was added to an antimony standard solution (1000 µg/mL), thereby preparing three or more calibration standard sample solutions having different concentrations. The calibration standard sample solutions contained 1-20 ng of antimony per mL of solution.

(3) Analysis operation: According to the following operating conditions 3, each of the standard solutions was analyzed by inductively coupled plasma mass spectrometry (ICP-MS) to obtain a calibration curve for antimony, and the amount of antimony in the analytical sample solution was measured using the obtained calibration curve.

<Operating Conditions 3>

Atomic weight: 206, 207 and 208 (selected and detected in a range in which there was no interference);

Plasma gas: argon (99.99 v/v % or more).

(4) The amount of antimony in an analytical sample solution was measured in the same manner as described in steps (1) to (3) above, except that each of liquid cosmetic raw materials 2 to 5 was used instead of liquid cosmetic raw material 1.

(5) The amount of cadmium in an analytical sample solution was measured in the same manner as described in steps (1) to (4) above, except that cadmium was used instead of antimony and that the following operating conditions 4 were used instead of operating conditions 3.

<Operating Conditions 4>

Wavelength: 193.759 nm (other characteristic wavelengths of arsenic may be selected if an interfering element is contained);

Plasma gas: argon (99.99 v/v % or more).

4-2. Comparison Between the Results of Quantitative Analysis According to Example of the Present Invention and the Results of Quantitative Analysis According to Comparative Example Table 7 below shows a comparison between the results of XRF analysis of antimony and cadmium in the analytical samples (liquid cosmetic raw materials 1 to 5) according to the Example of the present invention and the results of ICP-MS analysis of antimony and cadmium according to the Comparative Example.

TABLE 7

| | Content (ppm) | | | |
|---|---|---|---|---|
| | Antimony | | Cadmium | |
| Sample | XRF | ICP-MS | XRF | ICP-MS |
| Liquid cosmetic raw material 1 | 0 | 0 | 0 | 0 |
| Liquid cosmetic raw material 2 | 0 | 0 | 0.9 | 0.5 |
| Liquid cosmetic raw material 3 | 0 | 0 | 0 | 0 |
| Liquid cosmetic raw material 4 | 0 | 0 | 0 | 0 |
| Liquid cosmetic raw material 5 | 0 | 0 | 0.5 | 0 |

From the results in Table 7 above, it was shown that, compared to the method for ICP-MS analysis of antimony or cadmium, the method for analysis for antimony or cadmium according to the Example of the present invention was simple and convenient, because there was no pretreatment of the analytical sample, and it could quickly provide results, because the analysis time was short. In addition, it was shown that the analysis method according to the Example of the present invention would be suitable for analysis of samples having various matrices, because it comprises the step of correcting the matrix effect. Furthermore, it was found that the ICP-MS analysis results and the analysis results according to the Example of the present invention all had a relative standard deviation of less than 1%, indicating that the analysis method of the present invention can achieve accurate analysis.

Example 1-2: Selection of Optimum Conditions

In order to highly accurately analyze the lead, arsenic, antimony or cadmium contained in the sample to be analyzed, the following experiments were performed to determine the optimum conditions.

The optimum conditions were determined in the same manner as described in Example 1-1 above, except that the blank sample was selected as follows.

1-2. Selection of Blank Sample

In order to prepare a powdery standard sample with a suitable concentration, whether each of talc, sericite and mica is suitable as a blank sample for dilution was tested.

It is required that a blank sample does not contain lead, arsenic, antimony or cadmium and that other elements are not detected in the blank sample at positions similar to an energy level at which lead, arsenic, antimony or cadmium is detected. Analysis was performed in order to select a blank sample for powder sample measurement, which satisfies such requirements. As a result, it was found that talc would be suitable for use as a blank sample, because lead, arsenic, antimony or cadmium was not detected therein.

Example 2-3: Analysis of Lead and Arsenic in Powdery Sample

Using the optimum conditions selected in Example 1-2, the following experiments were performed in order to actually analyze lead present in various samples.

3-1. Analysis Instrument (XRF)

The X-ray fluorescence analyzer used in this Example was Xepos HE (Specto), and data processing was performed using X-Lap Pro program (Specto).

3-2. Standard Samples

As lead monoxide (INCI name: lead monoxide; chemical formula: PbO) used in a powdery standard sample, lead monoxide manufactured by ISHIZU PARM was used, and as arsenic trioxide (INCI name: arsenic trioxide; chemical formula: $As_2O_3$) used in a powdery standard sample, arsenic trioxide manufactured by ISHIZU PARM was used.

3-3. Quantitative Analysis of Lead and Arsenic in Powdery Cosmetic Raw Materials On powdery cosmetic raw materials, a method for quantitative analysis of lead and arsenic according to an embodiment of the present invention was performed.

First, about 6 mL of powdery cosmetic raw material 1 placed in a sample cup without bubbles was used as an analytical sample. In addition, 0.1 mL, 0.5 mL and 1 mL of the above-described lead standard sample were placed in 100 mL flasks, and then dispersed with 5-10% nitric acid solution according to marked lines, thereby preparing standard samples having different concentrations of 1 ppm, 5 ppm and 10 ppm. Energy peaks were measured on the analytical sample and the standard samples by an X-ray fluorescence analyzer under the following conditions, and based on the measured energy peaks, a standard calibration curve was determined using the linear squares method of Equation 1. According to a standard calibration method using the determined standard calibration curve, the concentration of lead in the analytical sample was measured. This procedure was also performed on powdery cosmetic raw materials 2 to 6 in the same manner.

In addition, the concentration of arsenic was analyzed in the same manner as the analysis of lead, except that a standard arsenic sample was used instead of the lead standard sample.

Figure 13:
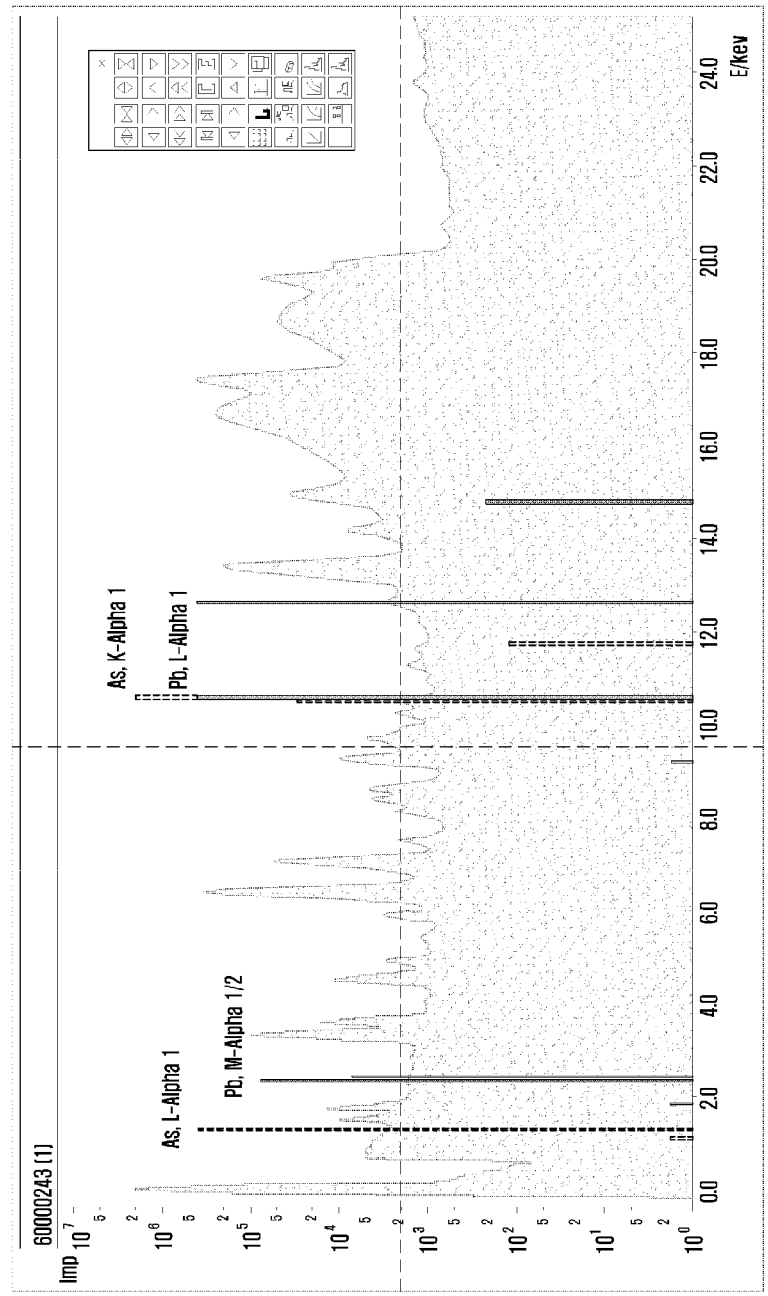
FIG. 13 shows X-ray spectra obtained by correcting values, measured by irradiating X-rays to powdery cosmetic raw materials, according to the step of correcting the absorption effect of an interfering element, in Example 2-3. The X-axis of the spectrum indicates energy level (keV), and the Y-axis indicates energy intensity.

The spectra of powdery cosmetic raw materials 1 to 5, which resulted from the analysis, are shown in FIG. 13, and the results of measuring the concentrations of lead and arsenic in powdery cosmetic raw materials 1 to 5 are shown in Table 8 below.

TABLE 8

| Sample | Concentration (ppm) | |
|---|---|---|
| | Lead | Arsenic |
| Powdery cosmetic raw material 1 (trade name: Z-COTE, manufactured by BASF) | 5.9 | 1.1 |
| Powdery cosmetic raw material 2 (Trade name: BTD-11S2, manufactured by KOBO) | 10.4 | 0 |
| Powdery cosmetic raw material 3 (trade name: Sericite JSSA, manufactured by Korea Synthetic Pearl) | 2.1 | 0 |
| Powdery cosmetic raw material 4 (trade name: Argel Red, manufactured by Arclay) | 0 | 1.3 |
| Powdery cosmetic raw material 5 (trade name: Palmac, manufactured by Acidchem) | 7.1 | 0 |

The standard calibration curves used to quantify the analyzed arsenic and lead were prepared in the range of 1.0-10 ppm. As can be seen in FIGS. 7 and 8, the prepared standard calibration curves had a correlation coefficient (R) of 0.999 or more, indicating that they had good linearity.

4-1. Quantitative Analysis of Lead and Arsenic in Powdery Cosmetic Products

In addition, the quantitative analysis of lead and arsenic in cosmetic products was performed in the same manner as described in Examples 3-1 to 3-3 above, and the results of the analysis are shown in Table 9 below.

TABLE 9

| Sample | Content (ppm) | |
|---|---|---|
| | Lead | Arsenic |
| Eye shadow 1 (trade name: Aritaum Monoeyes, manufactured by Amore Pacific) | 0 | 0 |
| Eye shadow 2 (trade name: Etudehouse Look At My Eyes, manufactured by: Etude) | 0 | 0 |
| Nail lacquer 1 (trade name: Aritaum Modi Nail Glam, manufactured by Amore Pacific) | 0 | 0 |
| Nail lacquer 2 (trade name: Innisfree Eco Nail Color, manufactured by Amore Pacific) | 0 | 0 |

5-1. Comparative Example: Quantitative Analysis of Lead and Arsenic in Powdery Cosmetic Raw Material by ICP-MS (1) Preparation of analytical sample solution: 0.2 g of powdery cosmetic raw material 1 as an analytical sample was placed in a vessel made of Teflon so as not to come into contact with the wall of the vessel. To decompose the analytical sample, 7 mL of nitric and 2 mL of hydrofluoric acid were placed in the vessel which was then covered with a lid and mounted in a microwave oven, and the analytical sample was decomposed under the following operating conditions 1 until it became colorless or yellow. The vessel was cooled to room temperature, and then the lid was opened. 20 mL of diluted (5→100) boric acid was placed in the vessel which was then covered with the lid mounted in the microwave oven, and fluorine was inactivated under the following operating conditions 2. The vessel was cooled to room temperature, and then the lid was carefully opened, and the decomposed material was transferred into a 100 mL flask. The vessel and the lid were washed with a suitable amount of distilled water, and distilled water was added to the decomposed material to a volume of 100 mL. If a precipitate existed, it was used after filtration. The resulting material was diluted 5-fold with distilled water, thereby preparing an analytical sample solution. In addition, a blank sample was prepared using 7 mL of nitric acid and 2 mL in the same manner as the preparation of the analytical sample solution.

TABLE 10

| Operating conditions 1 | Operating conditions 2 |
|---|---|
| Maximum power: 1000 W | Maximum power: 1000 W |
| Peak temperature: 200° C. | Peak temperature: 180° C. |
| Decomposition time: about 20 min | Decomposition time: about 10 min |

(2) Preparation of standard sample solutions: Diluted (2-100) nitric acid was added to a lead standard solution (1000 μg/mL), thereby preparing three or more calibration standard sample solutions having different concentrations. The calibration standard sample solutions contained 1-20 ng of lead per mL of solution.

(3) Analysis operation: According to the following operating conditions 3, each of the standard solutions was analyzed by inductively coupled plasma mass spectrometry (ICP-MS) to obtain a calibration curve for lead, and the amount of lead in the analytical sample solution was measured using the obtained calibration curve.

<Operating Conditions 3>

Atomic weight: 206, 207 and 208 (selected and detected in a range in which there was no interference);

Plasma gas: argon (99.99 v/v % or more).

(4) The amount of lead in an analytical sample solution was measured in the same manner as described in steps (1) to (3) above, except that each of powdery cosmetic raw materials 2 to 5 was used instead of powdery cosmetic raw material 1.

(5) The amount of arsenic in an analytical sample solution was measured in the same manner as described in steps (1) to (4) above, except that arsenic was used instead of lead and that the following operating conditions 4 were used instead of operating conditions 3.

<Operating Conditions 4>

Wavelength: 193.759 nm (other characteristic wavelengths of arsenic may be selected if an interfering element is contained);

Plasma gas: argon (99.99 v/v % or more).

5-2. Comparison Between the Results of Quantitative Analysis According to Example of the Present Invention and the Results of Quantitative Analysis According to Comparative Example Table 11 below shows a comparison between the results of XRF analysis of lead and arsenic in the analytical samples (powdery cosmetic raw materials 1 to 5) according to the Example of the present invention and the results of ICP-MS analysis of lead and arsenic according to the Comparative Example.

TABLE 11

| | Content (ppm) | | | |
|---|---|---|---|---|
| | Lead | | Arsenic | |
| Sample | XRF | ICP-MS | XRF | ICP-MS |
| Powdery cosmetic raw material 1 | 5.9 | 5.5 | 1.1 | 1.2 |
| Powdery cosmetic raw material 2 | 10.4 | 10.1 | 0 | 0 |

TABLE 11-continued

| | Content (ppm) | | | |
|---|---|---|---|---|
| | Lead | | Arsenic | |
| Sample | XRF | ICP-MS | XRF | ICP-MS |
| Powdery cosmetic raw material 3 | 2.1 | 2.3 | 0 | 0 |
| Powdery cosmetic raw material 4 | 0 | 0 | 1.3 | 1.1 |
| Powdery cosmetic raw material 5 | 7.1 | 7.4 | 0 | 0 |

From the results in Table 11 above, it was shown that, compared to the method for ICP-MS analysis of lead or arsenic, the method for analysis for lead or arsenic according to the Example of the present invention was simple and convenient, because there was no pretreatment of the analytical sample, and it could quickly provide results, because the analysis time was short. In addition, it was shown that the analysis method according to the Example of the present invention would be suitable for analysis of samples having various matrices, because it comprises the step of correcting the matrix effect. Furthermore, it was found that the ICP-MS analysis results and the analysis results according to the Example of the present invention all had a relative standard deviation of less than 1%, indicating that the analysis method of the present invention can achieve accurate analysis.

Example 2-4: Analysis of Antimony and Cadmium in Powdery Samples

Using the optimum conditions selected in Example 1-2, the following experiments were performed in order to actually analyze the antimony or cadmium present in various samples.

3-1. Analysis Instrument (XRF)

The X-ray fluorescence analyzer used in this Example was Xepos HE (Specto), and data processing was performed using X-Lap Pro program (Specto).

3-2. Standard Samples

As antimony (INCI name: antimony; atomic symbol: Sb) used in a powdery standard sample, antimony manufactured by Wako was used, and as cadmium oxide (INCI name: cadmium oxide; chemical formula: CdO) used in a powdery standard sample, arsenic trioxide manufactured by Aldrich was used.

3-3. Quantitative Analysis of Antimony and Cadmium in Powdery Cosmetic Raw Materials On powdery cosmetic raw materials, a method for quantitative analysis of antimony and cadmium according to an embodiment of the present invention was performed.

First, about 6 mL of powdery cosmetic raw material 1 placed in a sample cup without bubbles was used as an analytical sample. In addition, 0.1 mL, 0.5 mL and 1 mL of the above-described lead standard sample were placed in 100 mL flasks, and then dispersed with 5-10% nitric acid solution according to marked lines, thereby preparing standard samples having different concentrations of 1 ppm, 5 ppm and 10 ppm. Energy peaks were measured on the analytical sample and the standard samples by an X-ray fluorescence analyzer under the following conditions, and based on the measured energy peaks, a standard calibration curve was determined using the linear squares method of Equation 1. According to a standard calibration method using the determined standard calibration curve, the concentration of antimony in the analytical sample was mea- sured. This procedure was also performed on powdery cosmetic raw materials 2 to 6 in the same manner.

In addition, the concentration of cadmium was analyzed in the same manner as the analysis of antimony, except that a cadmium standard sample was used instead of the antimony standard sample.

Figure 14:
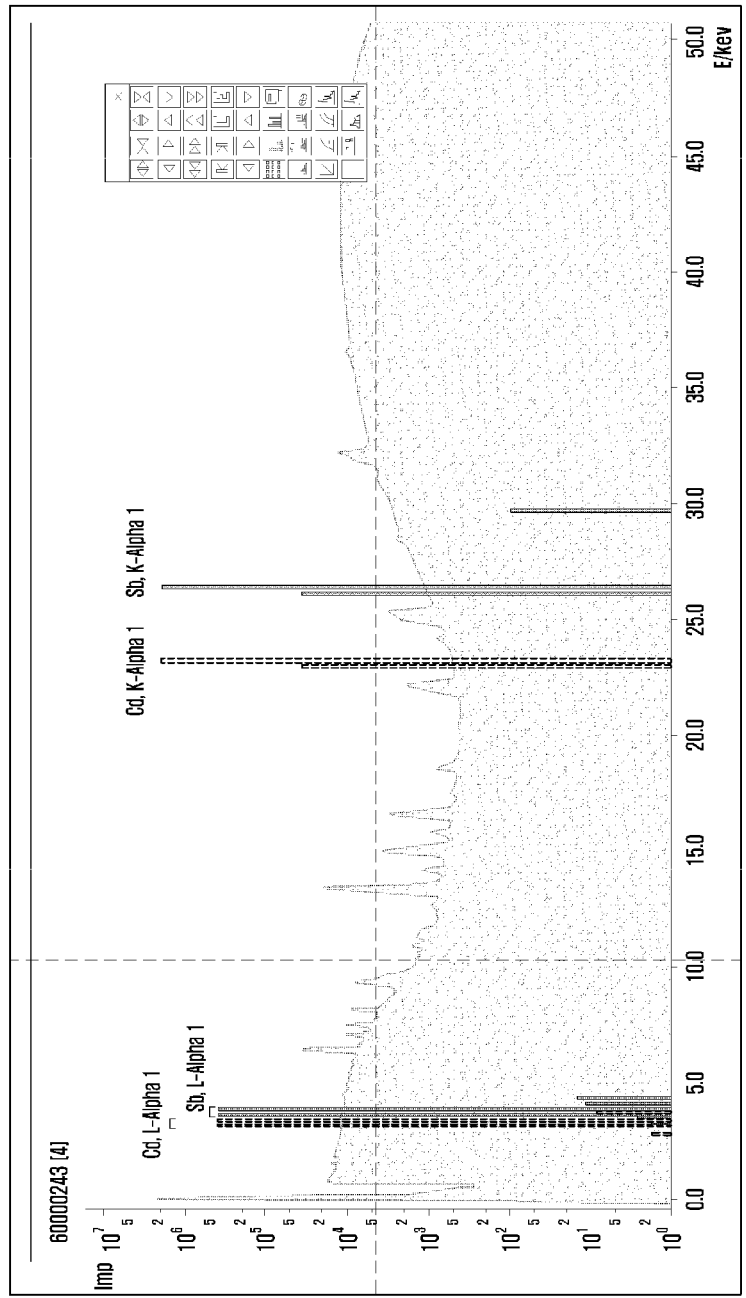
FIG. 14 shows X-ray spectra obtained by correcting values, measured by irradiating X-rays to powdery cosmetic raw materials, according to the step of correcting the absorption effect of an interfering element, in Example 2-4. The X-axis of the spectrum indicates energy level (keV), and the Y-axis indicates energy intensity.

The spectra of powdery cosmetic raw materials 1 to 5, which resulted from the analysis, are shown in FIG. 14, and the results of measuring the concentrations of antimony and cadmium in powdery cosmetic raw materials 1 to 5 are shown in Table 12 below.

TABLE 12

| | Concentration (ppm) | |
|---|---|---|
| Sample | Antimony | Cadmium |
| Powdery cosmetic raw material 1 (trade name: Z-COTE, manufactured by BASF) | 0 | 0 |
| Powdery cosmetic raw material 2 (trade name: BTD-11S2, manufactured by KOBO) | 0 | 0 |
| Powdery cosmetic raw material 3 (trade name: Sericite JSSA, manufactured by Korea Synthetic Pearl) | 0 | 1.73 |
| Powdery cosmetic raw material 4 (trade name: Argel Red, manufactured by Arclay) | 1.86 | 0 |
| Powdery cosmetic raw material 5 (trade name: Palmac, manufactured by Acidchem) | 0 | 0 |

The standard calibration curves used to quantify the analyzed antimony and cadmium were prepared in the range of 1.0-10 ppm. As can be seen in FIGS. 9 and 10, the prepared standard calibration curves had a correlation coefficient (R) of 0.999 or more, indicating that they had good linearity.

4-1. Quantitative Analysis of Antimony and Cadmium in Powdery Cosmetic Products

In addition, the quantitative analysis of antimony and cadmium in cosmetic products was performed in the same manner as described in Examples 3-1 to 3-3 above, and the results of the analysis are shown in Table 13 below.

TABLE 13

| | Content (ppm) | |
|---|---|---|
| Sample | Antimony | Cadmium |
| Eye shadow 1 (trade name: Aritaum Monoeyes, manufactured by Amore Pacific) | 0 | 0 |
| Eye shadow 2 (trade name: Etudehouse Look At My Eyes, manufactured by: Etude) | 0 | 0 |
| Nail lacquer 1 (trade name: Aritaum Modi Nail Glam, manufactured by Amore Pacific) | 0 | 0 |
| Nail lacquer 2 (trade name: Innisfree Eco Nail Color, manufactured by Amore Pacific) | 0 | 0 |
| Mud pack 1 (trade name: Aritaum Bamboo Charcoal Mud Pack, manufactured by Amore Pacific) | 0 | 0 |
| Mud pack 2 (trade name: Mud Rang Mud Pack, manufactured by Amore Pacific) | 0 | 0 |

5-1. Comparative Example: Quantitative Analysis of Antimony and Cadmium in Powdery Cosmetic Raw Materials by ICP-MS (1) Preparation of analytical sample solution: 0.2 g of powdery cosmetic raw material 1 as an analytical sample was placed in a vessel made of Teflon so as not to come into contact with the wall of the vessel. To decompose the analytical sample, 7 mL of nitric and 2 mL of hydrofluoric acid were placed in the vessel which was then covered with a lid and mounted in a microwave oven, and the analytical sample was decomposed under the following operating conditions 1 until it became colorless or yellow. The vessel was cooled to room temperature, and then the lid was opened. 20 mL of diluted (5→100) boric acid was placed in the vessel which was then covered with the lid mounted in the microwave oven, and fluorine was inactivated under the following operating conditions 2. The vessel was cooled to room temperature, and then the lid was carefully opened, and the decomposed material was transferred into a 100 mL flask. The vessel and the lid were washed with a suitable amount of distilled water, and distilled water was added to the decomposed material to a volume of 100 mL. If a precipitate existed, it was used after filtration. The resulting material was diluted 5-fold with distilled water, thereby preparing an analytical sample solution. In addition, a blank sample was prepared using 7 mL of nitric acid and 2 mL in the same manner as the preparation of the analytical sample solution.

TABLE 14

| Operating conditions 1 | Operating conditions 2 |
|---|---|
| Maximum power: 1000 W | Maximum power: 1000 W |
| Peak temperature: 200° C. | Peak temperature: 180° C. |
| Decomposition time: about 20 min | Decomposition time: about 10 min |

(2) Preparation of standard sample solutions: Diluted (2→100) nitric acid was added to an antimony standard solution (1000 μg/mL), thereby preparing three or more calibration standard sample solutions having different concentrations. The calibration standard sample solutions contained 1-20 ng of antimony per mL of solution.

(3) Analysis operation: According to the following operating conditions 3, each of the standard solutions was analyzed by inductively coupled plasma mass spectrometry (ICP-MS) to obtain a calibration curve for antimony, and the amount of antimony in the analytical sample solution was measured using the obtained calibration curve.

<Operating Conditions 3>

Atomic weight: 206, 207 and 208 (selected and detected in a range in which there was no interference);

Plasma gas: argon (99.99 v/v % or more).

(4) The amount of antimony in an analytical sample solution was measured in the same manner as described in steps (1) to (3) above, except that each of powdery cosmetic raw materials 2 to 5 was used instead of powdery cosmetic raw material 1.

(5) The amount of cadmium in an analytical sample solution was measured in the same manner as described in steps (1) to (4) above, except that cadmium was used instead of antimony and that the following operating conditions 4 were used instead of operating conditions 3.

<Operating Conditions 4>

Wavelength: 193.759 nm (other characteristic wavelengths of arsenic may be selected if an interfering element is contained);

2-3. Comparison Between the Results of Quantitative Analysis According to Example of the Present Invention and the Results of Quantitative Analysis According to Comparative Example Table 15 below shows a comparison between the results of XRF analysis of antimony and cadmium in the analytical samples (powdery cosmetic raw materials 1 to 5) according to the Example of the present invention and the results of ICP-MS analysis of antimony and cadmium according to the Comparative Example.

TABLE 15

| | Content (ppm) | | | |
| | Antimony | | Cadmium | |
| Sample | XRF | ICP-MS | XRF | ICP-MS |
|---|---|---|---|---|
| Powdery cosmetic raw material 1 | 0 | 0 | 0 | 0 |
| Powdery cosmetic raw material 2 | 0 | 0 | 0 | 0 |
| Powdery cosmetic raw material 3 | 0 | 0 | 1.73 | 1.7 |
| Powdery cosmetic raw material 4 | 1.86 | 1.6 | 0 | 0 |
| Powdery cosmetic raw material 5 | 0 | 0 | 0 | 0 |

From the results in Table 15 above, it was shown that, compared to the method for ICP-MS analysis of antimony or cadmium, the method for analysis for antimony or cadmium according to the Example of the present invention was simple and convenient, because there was no pretreatment of the analytical sample, and it could quickly provide results, because the analysis time was short. In addition, it was shown that the analysis method according to the Example of the present invention would be suitable for analysis of samples having various matrices, because it comprises the step of correcting the matrix effect. Furthermore, it was found that the ICP-MS analysis results and the analysis results according to the Example of the present invention all had a relative standard deviation of less than 1%, indicating that the analysis method of the present invention can achieve accurate analysis.

The invention claimed is:

1. A method for quantitative analysis of heavy metals, the method comprising:
   a step of preparing a blank liquid standard sample that is a nitric acid solution;
   a step of preparing two or more liquid standard samples having different concentrations by adding lead, arsenic, antimony or cadmium to the nitric acid solution;
   a step of selecting an interfering element, which has an energy level falling in a detected energy value range of lead, arsenic, antimony or cadmium, from among elements detected by irradiating X-rays to an analytical sample;
   a first step of irradiating X-rays to each of the prepared liquid standard samples having different concentrations, and then performing a deconvolution step so as to eliminate the effect of overlapping of energy peaks detected by irradiating the X-rays, thereby preparing a standard calibration curve; wherein the deconvolution step comprises correcting a detected energy peak of lead, arsenic, antimony or cadmium, among energy peaks detected by irradiating X-rays to the liquid standard samples having different concentrations, in the step of selecting the interfering element, from a detected energy peak of an overlapping interfering element; and
   a second step of irradiating X-rays to the analytical sample to detect an energy peak, and then measuring the concentration of lead, arsenic, antimony or cadmium in the analytical sample based on a detected energy peak value of the analytical sample by the prepared standard calibration curve according to a standard calibration method.

2. The method of claim 1, wherein the deconvolution step further comprises a step of correcting an absorption effect of the interfering element to remove an energy intensity value corresponding to an energy level range in which the detected energy peak of lead, arsenic, antimony or cadmium overlaps with the energy peak of the selected interfering element.

3. The method of claim 2, wherein the step of correcting the absorption effect of the interfering element further comprises a step of correcting the detected energy peak of lead, arsenic, antimony or cadmium by a Lucas-Tooth/Price algorithm.

4. The method of claim 3, wherein the step of correcting the detected energy peak of lead, arsenic, antimony or cadmium by the Lucas-Tooth/Price algorithm further comprises a step of collecting the detected energy peak of lead, arsenic, antimony or cadmium by the following Equation 1:

$$W_i = B_i + I_i \left[ k_i + \sum_j a_{ij} I_j \right]$$  Equation 1 wherein i is any one element of lead, arsenic, antimony and cadmium; j is an element interfering with i; $W_i$ is the mass-based concentration of lead, arsenic, antimony or cadmium in the sample; $I_i$ is the energy peak intensity of lead, arsenic, antimony or cadmium; $I_j$ is the energy peak intensity of elements other than lead, arsenic, antimony or cadmium; $k_i$ is the proportional constant of the mass-based concentration to the detected energy intensity of lead, arsenic, antimony or cadmium; $a_{ij}$ is the correction constant of the absorption effect of the detected energy peak of the interfering element for the detected energy peak of lead, arsenic, antimony or cadmium; and $B_i$ is a background constant corresponding to when the concentration of lead, arsenic, antimony or cadmium concentration is 0.

5. The method of claim 1, wherein the concentration of the nitric acid solution that is used in the step of preparing the blank liquid standard sample and the step of preparing the liquid standard samples having different concentrations is 5-10%.

6. The method of claim 1, wherein the detection of the energy peak in the deconvolution step and the step of measuring the concentration of lead, arsenic, antimony or cadmium in the analytical sample is performed by an X-ray fluorescence analysis method.

7. The method of claim 6, wherein X-rays that are used in the X-ray fluorescence analysis method are irradiated to the analytical sample or the standard samples through a polarizing plate comprising any one or more selected from the group consisting of molybdenum, aluminum, aluminum oxide, palladium, titanium, zirconium and cobalt.

8. The method of claim 1, wherein the method for quantitative analysis of heavy metals is a method for quantitative analysis of lead, and the interfering element is any one or more selected from the group consisting of thallium, arsenic, bismuth and polonium.

9. The method of claim 1, wherein the method for quantitative analysis of heavy metals is a method for quantitative analysis of arsenic, and the interfering element is any one or more selected from the group consisting of gallium, germanium, lead and selenium.

10. The method of claim 1, wherein the method for quantitative analysis of heavy metals is a method for quantitative analysis of antimony, and the interfering element is any one or more selected from the group consisting of tin, tellurium and iodine.

11. The method of claim 1, wherein the method for quantitative analysis of heavy metals is a method for quantitative analysis of cadmium, and the interfering element is any one or more selected from the group consisting of silver, indium and tin.

12. The method of claim 1, wherein the analytical sample is a cosmetic composition or a food composition.

13. A method for quantitative analysis of heavy metals, the method comprising:
a step of preparing talc powder as a blank powdery standard sample;
a step of adding lead, arsenic, antimony or cadmium to the talc powder to prepare two or more powdery standard samples having different concentrations;
a step of selecting an interfering element, which has an energy level falling in a detected energy value range of lead, arsenic, antimony or cadmium, from among elements detected by irradiating X-rays to an analytical sample;
a first step of irradiating X-rays to each of the prepared powdery standard samples having different concentrations, and then performing a deconvolution step so as to eliminate the effect of overlapping of energy peaks detected by irradiating the X-rays, thereby preparing a standard calibration curve; wherein the deconvolution step comprises correcting a detected energy peak of lead, arsenic, antimony or cadmium, among energy peaks detected by irradiating X-rays to the powdery standard samples having different concentrations, in the step of selecting the interfering element, from a detected energy peak of an overlapping interfering element; and
a second step of irradiating X-rays to the analytical sample to detect an energy peak, and then measuring the concentration of lead, arsenic, antimony or cadmium in the analytical sample based on a detected energy peak value of the analytical sample by the prepared standard calibration curve according to a standard calibration method.

14. The method of claim 13, wherein the concentration of a nitric acid solution that is used in the step of preparing the blank powdery standard sample and the steps of preparing the powdery standard samples having different concentrations is 5-10%.

15. The method of claim 13, wherein the lead, arsenic, antimony or cadmium that is used in the step of preparing the powdery standard samples having different concentrations is an oxide of lead, arsenic, antimony or cadmium.

* * * * *